US012779227B2

(12) United States Patent
Chauhan et al.

(10) Patent No.: US 12,779,227 B2
(45) Date of Patent: Nov. 3, 2026

(54) CONTROLLER FOR A PACING DEVICE

(71) Applicant: Ceryx Medical Limited, Cardiff (GB)

(72) Inventors: Ashok Singh Chauhan, Cardiff (GB); Graham John Fisher, Cardiff (GB)

(73) Assignee: CERYX MEDICAL LIMITED, Cardiff (GB)

( * ) Notice: Subject to any disclaimer, the term of this patent is extended or adjusted under 35 U.S.C. 154(b) by 372 days.

(21) Appl. No.: 18/263,013

(22) PCT Filed: Jan. 28, 2022

(86) PCT No.: PCT/GB2022/050241
§ 371 (c)(1),
(2) Date: Jul. 26, 2023

(87) PCT Pub. No.: WO2022/162388
PCT Pub. Date: Aug. 4, 2022

(65) Prior Publication Data
US 2024/0091542 A1 Mar. 21, 2024

(30) Foreign Application Priority Data
Feb. 1, 2021 (GB) ..................................... 2101363

(51) Int. Cl.
*A61N 1/365* (2006.01)

(52) U.S. Cl.
CPC ..... *A61N 1/36592* (2013.01); *A61N 1/36585* (2013.01)

(58) Field of Classification Search
None
See application file for complete search history.

(56) References Cited

U.S. PATENT DOCUMENTS

| | | | |
|---|---|---|---|
| 3,593,718 | A | 7/1971 | Krasner et al. |
| 4,567,892 | A | 2/1986 | Plicchi et al. |
| 4,576,183 | A | 3/1986 | Plicchi et al. |
| 4,596,251 | A | 6/1986 | Plicchi et al. |
| 4,930,518 | A | 6/1990 | Hrushesky |
| 5,690,688 | A | 11/1997 | Noren et al. |

(Continued)

FOREIGN PATENT DOCUMENTS

| | | | |
|---|---|---|---|
| GB | 2586987 | A | 3/2021 |
| JP | 07-088199 | H | 4/1995 |

(Continued)

OTHER PUBLICATIONS

Schafer, Carsten, et al., "Synchronization in the human cardiorespiratory system," The American Physical Society, Physical Review E, vol. 60, No. 1, Jul. 1999, pp. 857-870.

(Continued)

*Primary Examiner* — Mallika D Fairchild
(74) *Attorney, Agent, or Firm* — Ashurst Perkins Coie US LLP

(57) ABSTRACT

A controller for a pacing device, configured to; receive sensor data comprising respiratory data; determine a respiratory sinus arrhythmia, RSA, factor of a pacing signal based on the sensor data; determine a cardio-respiratory phase synchronisation, CRPS, factor of the pacing signal based on the sensor data; and provide the pacing signal for pacing a heart of a patient in accordance with the RSA factor and the CRPS factor.

18 Claims, 5 Drawing Sheets

(56) References Cited

U.S. PATENT DOCUMENTS

| | | | | |
|---|---|---|---|---|
| 5,964,788 | A * | 10/1999 | Greenhut ........... | A61N 1/36521 607/18 |
| 6,141,590 | A | 10/2000 | Renirie et al. | |
| 6,165,134 | A | 12/2000 | Marchesi | |
| 6,305,943 | B1 | 10/2001 | Pougatchev et al. | |
| 6,487,442 | B1 | 11/2002 | Wood | |
| 7,539,539 | B1 | 5/2009 | Bharmi | |
| 8,005,543 | B2 | 8/2011 | Libbus et al. | |
| 8,075,491 | B2 | 12/2011 | Bharmi | |
| 8,265,753 | B2 | 9/2012 | Higham et al. | |
| 8,483,833 | B2 | 7/2013 | Cho et al. | |
| 8,620,427 | B2 | 12/2013 | Libbus et al. | |
| 9,563,839 | B2 | 2/2017 | Nogaret | |
| 10,426,956 | B2 | 10/2019 | Williamson et al. | |
| 10,893,813 | B2 | 1/2021 | Libbus et al. | |
| 2004/0116820 | A1 | 6/2004 | Daum et al. | |
| 2009/0024176 | A1 | 1/2009 | Yun et al. | |
| 2012/0290032 | A1 * | 11/2012 | Cho ....................... | A61N 1/056 607/20 |
| 2014/0052209 | A1 | 2/2014 | Ternes et al. | |

FOREIGN PATENT DOCUMENTS

| | | | |
|---|---|---|---|
| JP | 2012236083 | A | 12/2012 |
| JP | 2012533351 | A | 12/2012 |
| WO | 9602185 | A1 | 2/1996 |
| WO | 2021048530 | A1 | 3/2021 |

OTHER PUBLICATIONS

International Search Report and Written Opinion mailed Mar. 31, 2022 for International Patent Application No. PCT/GB2022/050241.

Bartsch, Ronny P., et al., "Phase transitions in physiologic coupling," PNAS vol. 109, No. 26, 10181-10186, 2012.

C. P. Lau et al, "Rate-Responsive Pacing with a Pacemaker That Detects Respiratory Rate (Biorate) : Clinical Advantages and Complications", Clin. Cardiol. 11, 318-324 (1988).

H. Krause, "On the difference of cardiorespiratory synchronisation and coordination", Chaos 27, 093933 (2017); https://doi.org/10.1063/1.4999352.

M. Elstad et al., "Cardiorespiratory interactions in humans and animals: rhythms for life" Am J Physiol Heart Circ Physiol. Jul. 1, 2018;315(1):H6-H17. doi: 10.1152/ajpheart.00701.2017. Epub Mar. 9, 2018.

Bartsch, Ronny P., et al., "Coexisting Forms of Coupling and Phase-Transitions in Physiological Networks," V.M. Mladenov and p. C. Ivanov (Eds.): NDES 2014, CCIS 438, pp. 270-287, 2014.

JPO, Office Action for Japanese Application No. 2023-546201, mailed on Oct. 14, 2025, 9 pages with unofficial English translation.

* cited by examiner

CONTROLLER FOR A PACING DEVICE

CROSS REFERENCE TO RELATED APPLICATIONS

This patent document is a 371 National Phase Application of International Patent Application No. PCT/GB2022/050241, filed Jan. 28, 2022, which claims priority to United Kingdom Patent Application No. 2101363.6, filed on Feb. 1, 2021. The entire contents of the above noted applications are incorporated by reference as part of the disclosure of this document.

FIELD

The present disclosure relates to a pacing device, and in particular, although not exclusively, to a controller for a cardiac pacemaker for pacing the heart of a patient.

BACKGROUND

Pacing devices for applying a pacing signal to control the pacing of a patient's heart are commonly known in the art. Pacing devices, such as internal cardiac pacemakers, can include: one or more sensors for sensing physiological data relating to the patient; a controller for generating the pacing signal based on the physiological data; and electrodes for applying the pacing signal to the patient's heart. Such functional units are generally known in the art and therefore will not necessarily be discussed at length herein.

The one or more sensors of a pacing device may include a cardiac sensor. The cardiac sensor may comprise an electrode arrangement comprising cardiac electrodes which can be positioned in, on or about the heart to sense the cardiac electrical activity of one or more heart chambers. In some pacing devices, the electrodes may also be used to additionally provide the pacing signal to the heart. The electrodes may comprise cardiac pacing wires implanted into the heart, for example, in the right ventricle or the left ventricle.

The sensors of a pacing device may also include a respiratory sensor. The controller may utilize respiratory data from the respiratory sensor to determine the pacing signal. For example, a metabolic demand of a patient may be determined by monitoring the respiration of the patient. The respiratory sensor may comprise one or more of: an air flow sensor, a motion sensor, such as a thoracic abdominal motion sensor, a transthoracic impedance sensor comprising electrodes placed on the abdomen, a visual sensor for visualising movement of the abdomen or a strain gauge placed on the patient's chest. Respiratory data may also be determined by computer analysis of arterial waveforms. The respiratory data may include respiratory cycles determined from zero-crossings of the transthoracic impedance.

Known pacing devices may also receive activity data from an activity sensor. The activity sensor may comprise the cardiac sensor and/or the respiratory sensor. For example, activity data may be determined by monitoring the heart rate or respiratory rate of the patient. The activity sensor may also comprise one or more other sensors such as accelerometers, pulse oximeters, perspiration sensors, video sensors, temperature sensors or other sensors as known in the art. The controller may increase or decrease a rate of pulses of a pacing signal depending on the activity data.

The controller may comprise one or more processors, which may be one or more microprocessors. The one or more processors may operate as a state machine, a central pattern generator (CPG) or by any other implementation known in the art. The controller can generate on-demand atrial and/or ventricular pacing pulses as the pacing signal for application via the electrodes.

SUMMARY

According to a first aspect of the present disclosure there is provided a controller for a pacing device, configured to:

- receive sensor data comprising respiratory data;
- determine a respiratory sinus arrhythmia, RSA, factor of a pacing signal based on the sensor data;
- determine a cardio-respiratory phase synchronisation, CRPS, factor of the pacing signal based on the sensor data; and
- provide the pacing signal for pacing a heart of a patient in accordance with the RSA factor and the CRPS factor.

The controller may be configured to determine a patient activity level based on the sensor data. The controller may be configured to determine the RSA factor based on the patient activity level.

The sensor data may further comprise one or more of: cardiological data, pulse oximeter data, accelerometer data, body temperature data, perspiration data, camera data, an adenosine triphosphate, ATP, level and an adrenaline level.

The RSA factor may comprise one or more parameters of the pacing signal which provide a heart rate which is higher during an inspiration portion of a respiratory cycle than during an expiration portion of the respiratory cycle. The RSA factor may comprise one or more parameters of the pacing signal which define an extent that a heart rate is higher during an inspiration portion of a respiratory cycle than during an expiration portion of the respiratory cycle.

The CRPS factor may comprise one or more parameters of the pacing signal which provide heartbeat pulses with respiratory phase values that repeat over an integer number of respiratory cycles. A phase value of a heartbeat pulse may repeat over an integer number of respiratory cycles if it varies from a mean phase value by less than a CRPS threshold.

The controller may be configured to determine the CRPS factor based on the RSA factor.

The controller may be configured to provide the pacing signal in accordance with the RSA factor by controlling a timing of pulses in the pacing signal according to:

- a first rate when the respiratory data indicates inspiration; and
- a second rate when the respiratory data indicates expiration, wherein the first rate is greater than the second rate.

The sensor data may comprise cardiological data. The controller may be configured to determine a baseline heart rate from the cardiological data. The controller may be configured to set the first rate and second rate based on the baseline heart rate.

The controller may be configured to set a ratio of the first rate to the second rate based on the baseline heart rate.

The controller may be configured to determine a patient activity level based on the sensor data. The controller may be configured to set a ratio of the first rate to the second rate based on the patient activity level.

The controller may be configured to provide the pacing signal in accordance with the CRPS factor by controlling a timing of pulses in the pacing signal to correspond to the same set of respiratory phase angles in a repeat sequence over an integer number of respiratory cycles.

The controller may be configured to set the first rate and the second rate to control the timing of the pulses in the pacing signal to correspond to the same set of respiratory phase angles in a repeat sequence over an integer number of respiratory cycles.

The controller may be configured to determine a patient activity level based on the sensor data. The controller may be configured to determine the RSA factor based on the patient activity level. The controller may be configured to set a ratio of the first rate to the second rate based on the RSA factor. The controller may be configured to determine the CRPS factor as values of the first rate and second rate that provide the repeat sequence based on the ratio, a baseline heartrate of the sensor data and a respiratory rate of the respiratory data. The controller may be configured to provide the pacing signal based on the first rate and the second rate.

The controller may be configured to determine a first rate and a second rate that provide a modified baseline heart rate in the pacing signal to provide the repeat sequence.

The controller may be configured to adjust the ratio of the first rate to the second rate to determine the CRPS factor as values of the first rate and second rate that provide the repeat sequence.

The controller may be configured to determine the first rate and the second rate based on the ratio and the baseline heartrate by accessing a look-up table.

The controller may be configured to determine the CRPS factor to reduce the number of respiratory cycles over which the pacing signal repeats.

The controller may be configured to control the timing of the pulses in the pacing signal to correspond to the same set of respiratory phase angles within an acceptable deviation threshold.

The controller may be configured to determine a baseline number of heartbeats per respiratory cycle and/or baseline phase angles based on the cardiological data and the respiratory data. The controller may be configured to determine the set of respiratory phase angles based on the baseline number of heartbeats and/or the baseline phase angles.

The controller may be configured to determine the RSA factor and the CRPS factor based on a respiratory rate of the respiratory data.

The sensor data may comprise cardiological data and the controller may be configured to determine the RSA factor and the CRPS factor based on the cardiological data.

The controller may be configured to determine the RSA factor and the CRPS factor based on a heart rate of the cardiological data.

The controller may be configured to determine the RSA factor and the CRPS factor based on a beats per time interval value of the cardiological data.

The controller may be configured to determine the RSA factor and the CRPS factor based on a beats per breath value determined from the cardiological data and the respiratory data.

The respiratory data may comprise minute ventilation data.

According to a second aspect of the present disclosure there is provide a pacemaker system comprising:

any controller disclosed herein;

one or more sensors for providing the sensor data; and one or more pacing electrodes for applying the pacing signal to the heart of the patient.

According to a third aspect of the present disclosure there is provided a method for providing a pacing signal for pacing a heart of a patient, the method comprising:

receiving sensor data comprising respiratory data;

determining a respiratory sinus arrhythmia, RSA, factor of a pacing signal based on the sensor data;

determining a cardio-respiratory phase synchronisation, CRPS, factor of the pacing signal based on the sensor data; and providing the pacing signal for pacing the heart of the patient in accordance with the RSA factor and the CRPS factor.

According to a fourth aspect of the present disclosure there is provided a computer program product storing executable instructions for performing any method disclosed herein.

According to a further aspect of the disclosure, there is provided a method for providing a pacing signal for pacing a heart of a patient, the method comprising:

receiving sensor data comprising respiratory data;

setting, a pacing mode of the controller as:

a RSA mode; and/or a CRPS mode, dependent on the sensor data; and providing the pacing signal in accordance with the pacing mode.

While the disclosure is amenable to various modifications and alternative forms, specifics thereof have been shown by way of example in the drawings and will be described in detail. It should be understood, however, that other embodiments, beyond the particular embodiments described, are possible as well. All modifications, equivalents, and alternative embodiments falling within the spirit and scope of the appended claims are covered as well.

The above discussion is not intended to represent every example embodiment or every implementation within the scope of the current or future Claim sets. The figures and Detailed Description that follow also exemplify various example embodiments. Various example embodiments may be more completely understood in consideration of the following Detailed Description in connection with the accompanying Drawings.

BRIEF DESCRIPTION OF THE DRAWINGS

One or more embodiments will now be described by way of example only with reference to the accompanying drawings in which.

DETAILED DESCRIPTION

The present disclosure relates to a controller for a cardiac pacemaker and associated method of pacing. The method of pacing is derived from the inventor's observations of natural pacing in both healthy subjects and those with a range of physiological conditions under various levels of physical exertion. The proposed pacing scheme aims respond to physical demands on the subject by emulating the natural pacing observed in healthy subjects in such conditions.

The body's natural regulation of heartbeat is in phase with the breathing or respiratory cycle. Synchronisation between the heart and lungs is indicative of a healthy cardiorespiratory system. Coupling strength between the heart and lungs is one of the key factors behind increased synchronisation and decreased coupling strength—for instance through ageing and in patients with heart failure and other cardiorespiratory disorders—results in decreased synchronisation between the heart and lungs.

One example of synchronisation between the heart and lungs includes a reduction in heart rate during expiration (breathing out) and an increase in heart rate during inspiration (breathing in). This is referred to as respiratory sinus arrhythmia (RSA). The loss of RSA is a predictor of cardiovascular risk and a prognostic indicator for multiple diseases including heart failure.

Example pacing systems can be provided in order to artificially restore, maintain or enhance RSA to obtain a profile of a healthy individual. Applications GB 1913050.9 and PCT/GB2020/052149 disclose such systems and are hereby incorporated by reference in their entirety. Example systems may control the timing of stimulus signals (the pacing signal) according to a non-linear function. The non-linear function may be generated by a neuronal oscillator provided by a central pattern generator or a digital simulation.

Figure 1A:
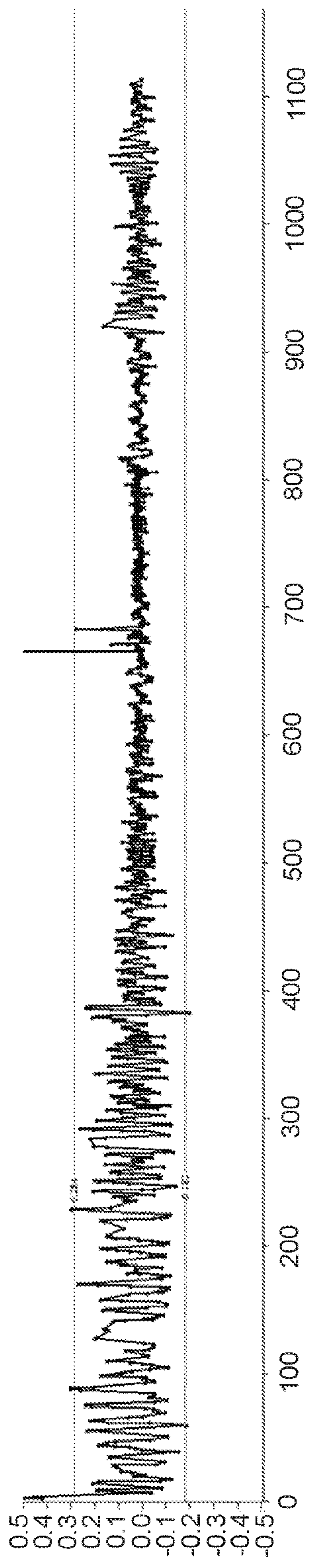
FIG. 1A illustrates a plot of respiratory sinus arrhythmia (RSA) amplitude against time for a healthy individual prior to, during and subsequent to physical exercise.
Figure 1B:
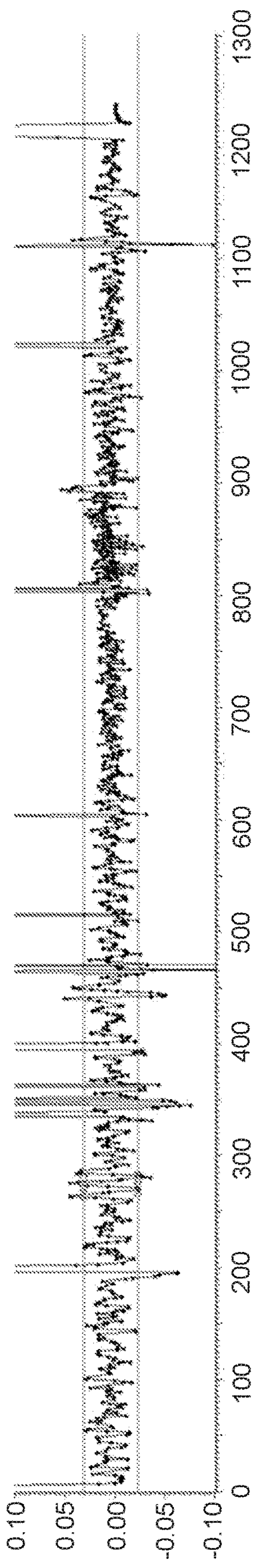
FIG. 1B illustrates a plot of RSA amplitude against time for an elderly individual prior to, during and subsequent to physical exercise

FIGS. 1A and 1B illustrate plots of RSA amplitude against time for respective first and second individuals prior to, during and subsequent to physical exercise. The data for FIG. 1A was acquired from a healthy individual (age 24+, height 180.5 cms, weight 88 Kg, BMI 27.0) while the data for FIG. 1B was acquired from an elderly, otherwise healthy, individual (age 64+, height 178 cms, weight 93 Kg, BMI 29.4). In both figures, the subjects are at rest at time=0 seconds. In FIG. 1A, exercise onset occurs at time=180 seconds and the exercise period ends at time=800 seconds. In FIG. 1B, exercise onset occurs at time=300 seconds and the exercise period ends at time=800 seconds FIG. 1A indicates a healthy RSA level of ~0.5 Hz peak to peak amplitude for the first individual at rest. The first individual was subject to a gradually increasing intensity of exercise from 180 s to 800 s. The RSA amplitude remains high before the onset of exercise (i.e. before 180 s) and during the initial phase of exercise (i.e. between 180 s and 400 s). The RSA amplitude decreases, to less than 0.1 Hz, at higher intensity of exercise (i.e. between 500 s and 800 s). In the recovery time (i.e. after 800 s), the RSA amplitude starts increasing in amplitude again.

FIG. 1B indicates an unhealthy level of RSA of ~0.05 Hz peak to peak amplitude for the second individual at rest. As seen in the figure, the RSA amplitude also decreases following exercise onset and recovers again following the end of exercise. The trend in FIG. 1B is less obvious than that in FIG. 1A because the resting level of RSA is relatively low to begin with so there is a high signal to noise ratio.

FIGS. 1A and 1B illustrate that RSA decreases during physical activity for individuals with both healthy and unhealthy cardiorespiratory systems. RSA amplitude is high in healthy subjects at rest and decreases with increased exertion levels. Individuals with an unhealthy cardiorespiratory system tend to have lower RSA amplitude, even at rest, which further decreases with increased exertion.

Figure 2A:
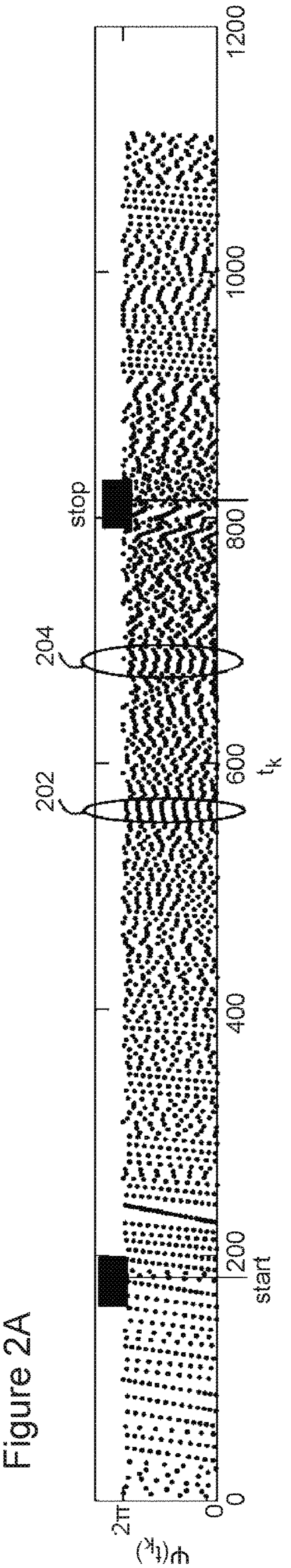
FIG. 2A illustrates a synchrogram plot corresponding to the RSA plot of FIG. 1A.
Figure 2B:
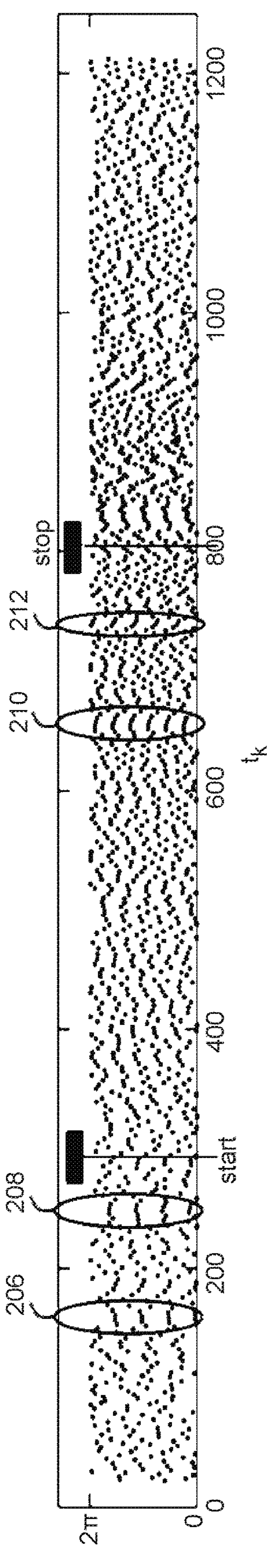
FIG. 2B illustrates a synchrogram plot corresponding to the RSA plots of FIG. 1B.

FIGS. 2A and 2B illustrate synchrogram plots corresponding to the respective RSA plots of FIGS. 1A and 1B. A synchrogram plots heartbeat instances, in time, on the x-axis with respect to a respiratory phase on the y-axis. Here, respiratory phase defines an instantaneous phase angle of the respiratory cycle, relative to the start of the respiratory cycle. The respiratory phase varies or cycles between 0 and 2n radians during a single respiratory cycle in the same way as a conventional oscillating system.

For the first individual (FIG. 2A), a regular pattern of heartbeats with approximately 12 heartbeats per respiratory cycle can be seen during the period prior to exercise onset at 180 seconds. This regular heart rate and a high number of heartbeats per respiratory cycle correspond to the period of high amplitude RSA. As the exercise progresses and the RSA amplitude decreases a second type of synchronisation becomes identifiable in the synchrogram plot—cardio-respiratory phase synchronisation (CRPS). Regions of CRPS 202, 204 can be seen in the synchrogram plot as regions in which the respiratory phase of corresponding heartbeats in adjacent respiratory cycles have a substantially constant phase. In other words, the heart beats or pulses at the same repeating phase angles in consecutive respiratory cycles. The regions of CRPS 202, 204 can be identified in the synchrogram plot as substantially horizontal lines or plateaus formed by the heartbeat instances in adjacent respiratory cycles. CRPS is not necessarily limited to heart beats having the same phase angles in consecutive or adjacent respiratory cycles and that the repeat sequence of phase angles may extend over an integer number of respiratory cycles (for example, up to one of 2, 3, 4, 6 or more respiratory cycles). As explained below in relation to FIGS. 2C and 2D, CRPS tends to be continually present subject to interruptions in the respiratory cycle due to ingestion, yawning, hiccups etc. Therefore, FIG. 2A includes regions of CRPS that are not immediately identifiable because the heart rate is relatively low (for example prior to exercise onset) and/or because the repeat sequence of phase angles is over a number of respiratory cycles.

For the second individual (FIG. 2B), there are identifiable regions of CRPS 206, 208, 210, 212 both prior to exercise onset and during exercise. There are approximately four to five heartbeats per respiratory cycle prior to exercise onset increasing to five to six beats per respiratory cycle during exercise.

Figure 2C:
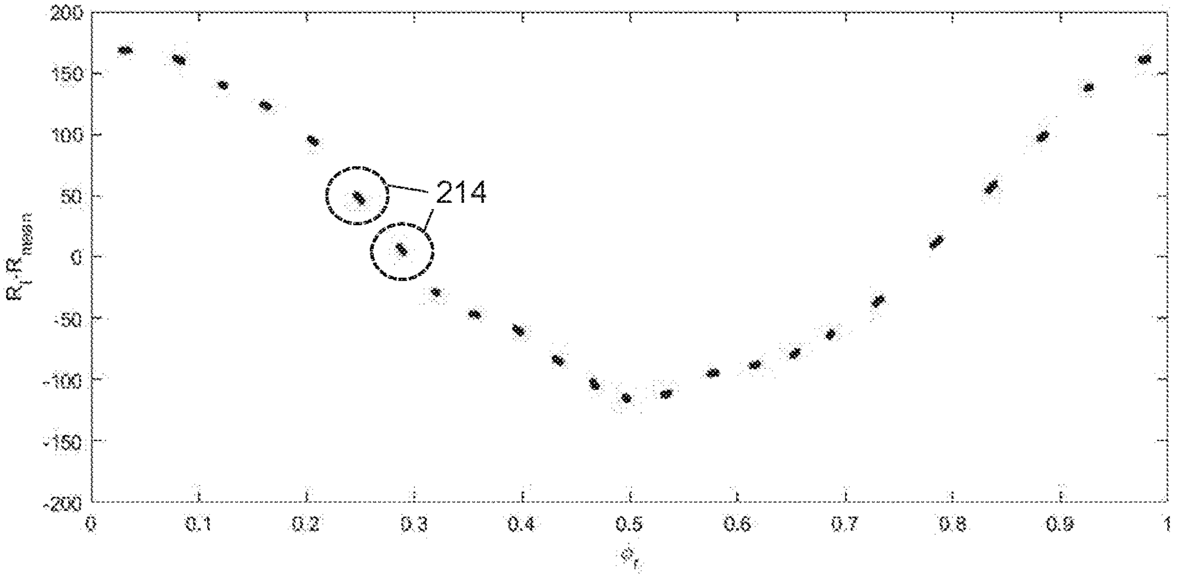
FIG. 2C illustrates simulated cardio-respiratory data for a healthy heart exhibiting RSA and an unhealthy heart exhibiting no RSA.
Figure 2D:
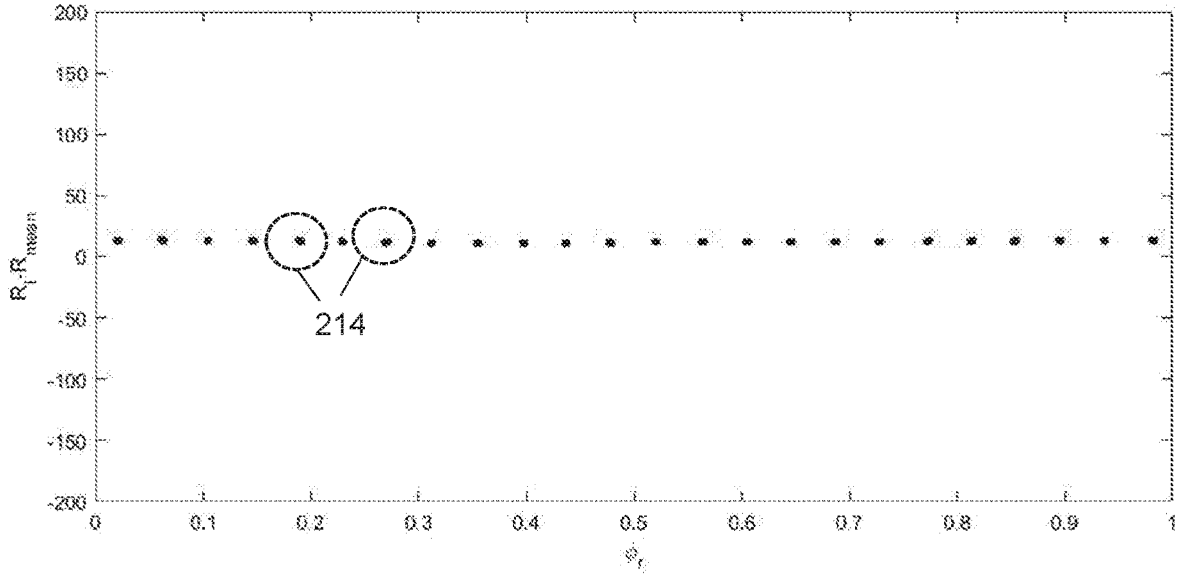
FIG. 2D illustrates simulated cardio-respiratory data for an unhealthy heart that does not exhibit RSA.

FIGS. 2C and 2D respectively illustrate simulated cardio-respiratory data for a healthy heart exhibiting RSA and an unhealthy heart exhibiting no RSA. The cardio-respiratory data is plotted with phase of the respiratory cycle plotted on the horizontal axis (on a scale of 0 to 1 equivalent to 0 to 2n radians in the plots of FIGS. 2A and 2B) and R-wave deviation from the mean plotted on the vertical axis. Here, R-wave deviation refers to the deviation of R-R interval (or heartbeat period) from the mean R-R interval.

RSA can be clearly seen in FIG. 2C as a cycle in the R-wave deviation from a positive value to a negative value and back to a positive value. In contrast, FIG. 2D sees no variation in the R-wave deviation indicative of an absence of RSA.

Heart beats are shown on each plot of FIGS. 2C and 2D for multiple respiratory cycles and the data can be seen to form clusters 214. The clusters define a plurality of heart-beats occurring at the same respiratory phase over a number of respiratory cycles. In other words, the data illustrates CRPS for both the heart exhibiting RSA and the heart where RSA is absent. In both examples of FIGS. 2C and 2D the repeat sequence of phase angles occurs over more than one respiratory cycle, as evidenced by the large number of beats per respiratory cycle. For example, every other illustrated cluster 214 may correspond to a first respiratory cycle with the intervening clusters 214 corresponding to a second respiratory cycle, if the repeat sequence is over two respiratory cycles.

FIGS. 2A to 2D illustrate that both healthy and unhealthy hearts naturally tend towards exhibiting CRPS 202-210 regardless of the presence of RSA. FIG. 2A illustrates that CRPS is present in a healthy individual when the cardio-respiratory system is stressed during exercise, FIG. 2B illustrates that CRPS is present in an unhealthy cardiorespiratory system both at rest and during exercise and FIGS. 2C and 2D illustrate that CRPS is present in both the presence and absence of RSA.

Therefore, a heart may be considered as having three operating states: (i) unsynchronised with no CRPS and no RSA, particularly prevalent when the heart is under severe stress and/or there is an interruption in breathing; (ii) phase synchronised CRPS with no RSA, particularly prevalent when a person is performing an activity such as exercise; and (iii) phase synchronised CRPS with RSA, prevalent when a healthy heart is at rest or performing a moderate amount of activity relative to an underlying fitness. In various embodiments of the present disclosure, controllers for pacing devices are provided which may tend to move the heart state upwards from state (i) to state (iii) depending on the demand on the heart (activity, etc.) relative to an underlying fitness and/or tissue health.

The present disclosure provides controllers for pacing devices that account for the two types of natural cardio-respiratory synchronisation in healthy individuals— RSA at rest (and low levels of activity relative to an individual's fitness level) and a continual tendency towards CRPS. The present disclosure provides controllers for pacing systems that can provide a pacing signal for pacing a heart of a patient with an RSA component while maintaining CRPS. Specifically, the controller can determine: (i) a RSA factor of a pacing signal for inducing RSA in the patient; and (ii) a cardio-respiratory phase synchronisation, CRPS, factor of the pacing signal for inducing CRPS in the patient. The controller can determine the two factors based on sensor data relating to the patient. The sensor data includes respiratory data for aiding the synchronisation of the timing of the pacing signal in accordance with the RSA factor and the CRPS factor.

In some examples, the controller the controller may determine the RSA factor based on a patient activity level indicated by the sensor data. The controller may reduce the amount of RSA in the pacing signal in proportion to (or as a non-linear function of) an increase in activity level. As the activity level increases beyond an upper (safe) limit for a patient's individual fitness/tissue health, the controller may determine the RSA factor as zero (or one depending on the implementation) to provide a pacing signal that does not induce any RSA. In this way, the controller may not attempt to induce RSA when sensor data indicates that a cardio-respiratory system is under temporary increased stress, such as during intense exercise or other strenuous activity. As a result, the controller provides a pacing signal that advantageously replicates the natural pacing of a healthy cardio-respiratory system at rest and as a stress level is increased.

The controller can advantageously provide a pacing signal for inducing both RSA and CRPS. In this way, the controller may induce both RSA and CRPS when sensor data indicates that the cardiorespiratory system is not under increased stress, such as when the patient is at rest or undertaking moderate levels of activity.

In some examples, the controller may also determine the RSA factor and CRPS factor to induce neither RSA nor CRPS if sensor data indicates that the patient is under a severe level of stress beyond a safety threshold. The controller may also induce neither type of synchronisation during a calibration mode or free-running mode during which the controller may determine a baseline health or fitness of a patient based on a baseline set of sensor data. For example, the controller may determine a patient's underlying fitness/disease state by entering a diagnosis mode during which the patient undertakes a known activity, for example a 6 minute walk test. The controller may then determine a baseline mean pulse rate and level of RSA and CRPS factor adjustment to apply to the pacing signal per unit change in respiration rate. In the calibration mode, the controller may determine a set of cardio-respiratory relationship data defining relationships between cardiological sensor data and respiratory sensor data over a range of activity levels. For example, the controller may be configured to determine, for a particular patient, an ideal heart rate as a function of non-cardiological sensor data based on the relationship between the cardiological sensor data and the non-cardiological sensor data during the calibration mode.

A pacing device implementing a controller as disclosed herein, can slow down disease progression, reverse damage to heart muscle (remodelling of the myocardium), or obtain better cardiac pumping function from the remaining viable cardiac muscle in order to improve quality of life outcomes for the subject of the cardiac device.

Figure 3:
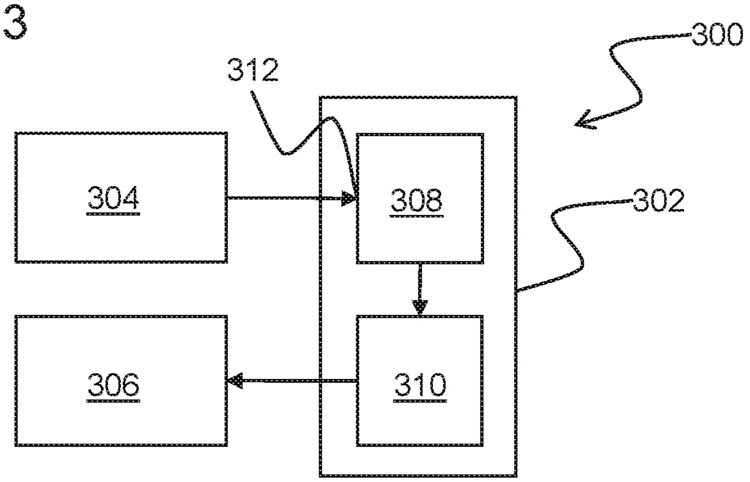
FIG. 3 illustrates a schematic block diagram of a cardiac pacemaker system.

FIG. 3 illustrates a schematic block diagram of a cardiac pacemaker system 300 comprising a pacing device 302 having a controller 308 according to one or more embodiments of the present disclosure. The cardiac pacemaker system 300 comprises a cardiac pacing device 302, one or more sensors 304 and one or more pacing electrodes 306. The pacing system 300 is an electronic device for artificially inducing both: (i) the biological RSA process present in a healthy individual at rest; and (ii) the biological CRPS process that all hearts tend towards in the absence of respiratory or cardiac interruption. The provision of such devices may also prove advantageous, where some RSA and/or CRPS occurs naturally in the patient, to apply RSA and/or CRPS at higher levels or more regularly than naturally occurring using such a device.

The one or more sensors 304 may comprise a respiratory sensor for providing respiratory data as sensor data to the controller 308. The respiratory sensor may comprise an electromyography sensor or a chest impedance sensor, for example. The respiratory sensor may be configured to sense a signal indicative of respiration of the subject. The one or more sensors 304 may further comprise a cardiac sensor and/or an activity sensor for providing respective cardiological data and/or activity data relating to the subject. Use of such data by the controller 308 is discussed further below.

The respiratory data may comprise minute ventilation data. The controller may be configured to determine a minute ventilation parameter based on the minute ventilation data. Minute ventilation (VE) is defined as the volume of gas inhaled (inhaled minute ventilation) or exhaled (exhaled minute ventilation) from a person's lungs per minute. Minute ventilation can be written as:

$$VE=TV \times f$$

where, TV=tidal volume f=frequency of respiration

Tidal volume is a measure of the volume of air displaced between normal inhalation and exhalation without extra effort. Minute ventilation (VE) is proportional to respiratory effort and the frequency of respiration. The controller 308 may determine the activity level based on the minute ventilation parameter.

Any of the one or more sensors 304 may be provided by conventional sensors used in the art (such as those described in the background section above) and may include mechanisms or adhesives for coupling the one or more sensors 304 to the subject. The cardiac pacing device 302 may be configured to communicate with the one or more sensors 304 via a wireless or wired communications link. For example, a near-field communications link could operate through tissue of the patient so that one of i) the cardiac pacing device 302 and ii) the one or more sensors 304 is provided internally and the other is provided externally.

The one or more pacing electrodes 306 may be provided by conventional pacing electrodes that are configured to apply an electrical stimulus to the subject. The one or more pacing electrodes 306 may comprise a mechanism or adhesive for attaching the one or more pacing electrodes 306 to the subject. The one or more pacing electrodes 306 may also provide the functionality of a cardiac sensor.

The cardiac pacemaker device 302 comprises a controller 308 and an electrical stimulus generator 310. The controller 308 may comprise one or more processors. The one or more processors may operate as a state machine, a central pattern generator (CPG) or by any other implementation known in the art. The controller 308 can generate on-demand atrial and/or ventricular pacing pulses as a stimulus signal for application via the pacing electrodes 306.

The controller 308 is configured to receive sensor data including the respiratory data from the one or more sensors 304 at a sensor signal input 312. The controller 308 is configured to determine a RSA factor and a CRPS factor of a pacing signal based on the sensor data and provide the pacing signal for pacing a heart of the patient in accordance with the RSA factor and the CRPS factor. The controller 308 may provide the pacing signal to the electrical stimulus generator 310 which provides a corresponding stimulus signal to the heart of the patient via the one or more pacing electrodes 306. In other examples, the electrical stimulus generator may form part of the controller 308 and the controller may provide the pacing signal as a stimulus signal directly to the one or more pacing electrodes 306. The pacing signal and stimulus signal may comprise a sequence of pulses with a timing corresponding to a timing of an induced heartbeat in the heart of the patient.

The cardiac pacing device 302 may be an implantable device. For example, the cardiac pacing device 302 may have a housing, which may be biologically inactive, or non-reactive. The housing may have dimensions of 10 cm or less by 5 cm or less, for example. The cardiac pacing device 302 may include a power source to power the device 302.

The electrical stimulus generator 310 is configured to generate the stimulus signal based on the pacing signal provided by the controller 308. The electrical stimulus generator 310 may be provided by conventional pulse generation hardware, for example, and is configured to provide the stimulus signal to the one or more pacing electrodes 306.

The controller 308 may be provided by hardware, software or a combination of hardware and software. In one example, the controller 308 may be provided as software modules that are executed by hardware, for example.

According to the first aspect the controller 308 of the pacing device 302 is configured to receive sensor data comprising respiratory data. The controller 308 may receive the sensor data from the one or more sensors 304. The controller 308 is configured to determine a RSA factor of a pacing signal based on the sensor data and determine a CRPS factor of the pacing signal dependent on the sensor data, and provide the pacing signal for pacing a heart of a patient in accordance with the RSA factor and the CRPS factor.

As described above, the controller 308 may determine the RSA factor and accordingly provide a pacing signal to artificially induce RSA in the patient. The pacing signal may comprise a sequence of pulses, with each pulse for inducing a heartbeat in the patient. The controller 308 may control the timing of the pulses in the pacing signal in accordance with the RSA factor based on timing information in the respiratory data. For example, the controller 308 may control the timing of the pulses with a first rate when the respiratory data indicates inspiration and with a second rate when the respiratory data indicates expiration, wherein the first rate is greater than the second rate. For example, the first rate may be greater than the second rate by 0.1 to 1.0 Hz, preferably 0.2 to 0.5 Hz. In another example the first rate may be increased by 10 to 15 beats per minute (BPM) for an upper level of RSA. An upper level may correspond to a 15 BPM increase on a 100 BPM heart rate. A lower level may correspond to a 15 BPM increase on a 45 BPM heart rate.

Alternatively, the first rate may be scaled relative to the second rate. For example, the first rate may be 5 to 100% higher than the second rate. The RSA factor may correspond to a ratio between the first rate and the second rate.

The sensor data may further comprise cardiological data relating to the patient's heart. The controller 308 may receive the cardiological data from a cardiac sensor. The cardiac sensor may comprise the pacing electrodes 306. The controller 308 may also determine the RSA factor based on timing information in the cardiological data. For example, a baseline heart rate may be determined from the cardiological data and the first rate and second rate may be based on the baseline heart rate.

As discussed further below, the sensor data may further comprise activity data representative of a patient activity level. The controller 308 may determine the RSA factor based on the activity data. For example, the controller 308 may scale the first rate and/or the second rate based on an activity level indicated by the activity data.

The controller 308 may scale a magnitude of the RSA factor (first rate divided by second rate) based on any combination of: the respiratory data, the cardiology data or the patient activity level. For example, the controller may adjust the magnitude of the RSA factor with increasing heart rate, respiration rate and/or patient activity level. The controller may further scale the magnitude of the RSA factor based on one or more of: age, fitness level and co-morbidities.

The controller 308 may determine the CRPS factor to induce or maintain CRPS in the patient. The controller 308 may determine the CRPS factor based on the timing information in the respiratory data. For example, the controller 308 may control the timing of the sequence of pulses in the pacing signal to occur at the same set of phase angles for successive respiratory cycles or over an integer number of respiratory cycles. In this way, the controller 308 can control the timing of the pulses such that a respiratory phase of corresponding heartbeats in adjacent respiratory cycles or adjacent sets of respiratory cycles is substantially constant. Here, substantially constant may be defined as a variation in phase angle between corresponding heartbeats in adjacent respiratory cycles being less than a CRPS threshold, for example 0.1, 0.2, 0.3, 0.4 or 0.5 radians.

The controller 308 may also determine CRPS factor based on timing information in the cardiological data. For example, the controller 308 may determine a baseline heartbeats per respiratory cycle from the cardiological data and set the phase angles of the pulses based on the baseline heartbeats per respiratory cycle. The controller may also determine a set of baseline phase angles and set the phase angles of the pulses based on the set of baseline phase angles. The baseline phase angles may correspond to average phase angles over a number of adjacent respiratory cycles or a number of adjacent sets of respiratory cycles. As a simplified example with no RSA present, the controller 308 may determine a baseline heartbeats per respiratory cycle of 5.5 beats per respiratory cycle and average phase angles of 0, 2n/11, 4n/11, 6n/11, 8n/11, 10n/11, n/11, 3n/11, 5n/11, 7n/11 and 9n/11 over adjacent sets of two respiratory cycles. The controller 308 may control the timing of the pulses of the pacing signal in accordance with the CRPS factor to maintain a predetermined number (e.g. 5.5) beats per respiratory cycle and the average phase angles for each respiratory cycle. The CRPS factor may comprise one or more parameters that provide the repeating set of respiratory phase angles over an integer number of respiratory cycles. For example, the CRPS factor may comprise any of: the set of respiratory angles; a respiratory angle period corresponding to a difference between consecutive respiratory phase angles in the set of respiratory angles; and values of the first rate and the second rate that will provide the set of respiratory angles or an offset set of respiratory angles with the same respiratory angle period as the set of respiratory angles with a fixed temporal offset.

In one or more examples, the controller may determine the CRPS factor based on the RSA factor. For example, the controller may determine the RSA factor based on the patient activity level. The controller may then determine a ratio of the first rate (for the pacing signal during inspiration) to the second rate (for the pacing signal during expiration) based on the RSA factor. For example, the controller may set the ratio equal to the RSA factor. The dependence of the RSA factor on the activity level may be calibrated or predetermined on a patient by patient basis and may depend on factors such as age, BMI, health conditions etc. The controller may determine the CRPS factor based on the ratio or the RSA factor. The controller may determine the CRPS factor based on the ratio (RSA factor) and a measured baseline heart rate from cardiological data of the sensor data.

The controller may set the first rate and the second rate of the pacing signal such that the baseline (average) heartrate is maintained and with the determined ratio/RSA factor. However, in some examples, this may result in no CRPS because the resulting values of the first and second rate do not result in a repeat sequence of respiratory phase values over an integer number of respiratory cycles or in CRPS which repeats only over a very large number of respiratory cycles. Therefore, the controller may adjust the ratio determined based on the RSA factor to determine the CRPS factor as values of the first rate and the second rate that will result in a repeat sequence over a reduced number of respiratory cycles. Alternatively, or in addition, the controller may adjust the first rate and or the second rate (the CRPS factor) to provide a pacing signal with a baseline (average) pulse rate that differs from the measured baseline heartrate such that that will result in a repeat sequence over a reduced number of respiratory cycles.

The controller may define a set of stable operating modes with a fixed CRPS factor with a fixed first and second rate. The CRPS factor may correspond to repeat sequences that occur over only a few respiratory cycles (such as 1, 2, 3 or 4 respiratory cycles). Each stable operating mode may correspond to a range of baseline heart rates and a range of RSA factors. For example, a first stable operating mode may correspond to a first rate of 6.0 beats per respiratory cycle and a second rate of 5.0 beats per respiratory cycle. The ratio of the first rate to the second rate is 1.2. The baseline heartrate is 5.5 beats per respiratory cycle and the phase angles will repeat over each set of two respiratory cycles. The controller may determine a RSA factor as 1.19 based on a patient activity level and measure a baseline heartrate of 5.48. The controller may select the first stable operating mode because the RSA factor and the baseline heartrate fall within a threshold range of values of the first stable operating mode. In this way, the controller determines the CRPS factor as the stable operating mode with a range encompassing the determined RSA factor and measured baseline heartrate. The controller may comprise a lookup table with a set of CRPS factors or stable operating modes corresponding to ranges of RSA factors and baseline heartrates. The controller may access the lookup table to determine the CRPS factor. The lookup table may be predetermined based on historical patient data, including for example observed heart rate data, or modelled data.

In operation, there may be changes in the timing of heart beats from beat to beat due to biological processes. However, during CRPS, the short-term averaged phase values will tend to repeat over an integer number of respiration periods. In other words, a phase value of a heartbeat pulse may be considered to repeat over an integer number of respiratory cycles if it varies from a mean phase value by less than a CRPS threshold.

The controller may be configured to monitor two different short-term averages to determine if the pacing signal should move to a new stable operating mode. Firstly, the controller may be configured to monitor a difference between the short-term mean heartrate (for example over a short time period such as five to ten seconds, over one, two, three or more respiratory cycles, or over an integer number of heartbeats) generated by the device and an ideal baseline heartrate (determined using any of the methods described above, for example based on respiratory data and the relationship data determined in the calibration mode). If the difference exceeds a threshold for a predetermined duration of time, the controller may set the pacing parameters to correspond to the next stable operating mode. In this way, the controller may maintain a stable operating condition whilst the short-term average heartrate is substantially equal to an ideal heartrate, determined from the non-cardiological data and the calibration data, and change to a new operating condition when an average heart-rate is persistently above a CRPS error threshold.

As a second option, the controller may monitor a short-term mean phase value difference. For a good match between the pacing pattern and respiration the short term mean should be around 0 (that is, phase locked but with jitter and biological processes causing the mean difference to vary. A short term mean phase difference may be measured in a period of less than 1, 2 or 5 cardiac cycles, for example, or for a predetermined period. If the difference exceeds a threshold for the predetermined period and in a biased direction (which may be consistently above a positive threshold), the controller may move to the next stable operating mode.

The controller may integrate or long term filter the cardiological data to determine average values over the predetermined period. In this way, the controller may maintain a stable operating condition whilst the short-term average phase-value is substantially constant and change to a new operating condition when an average phase difference is persistently above a CRPS error threshold. The controller may include a phase-sensitive detection capability based on the changes in respiration window. The controller may implement a neuron network for such a phase-sensitive detection capability.

Figure 4:
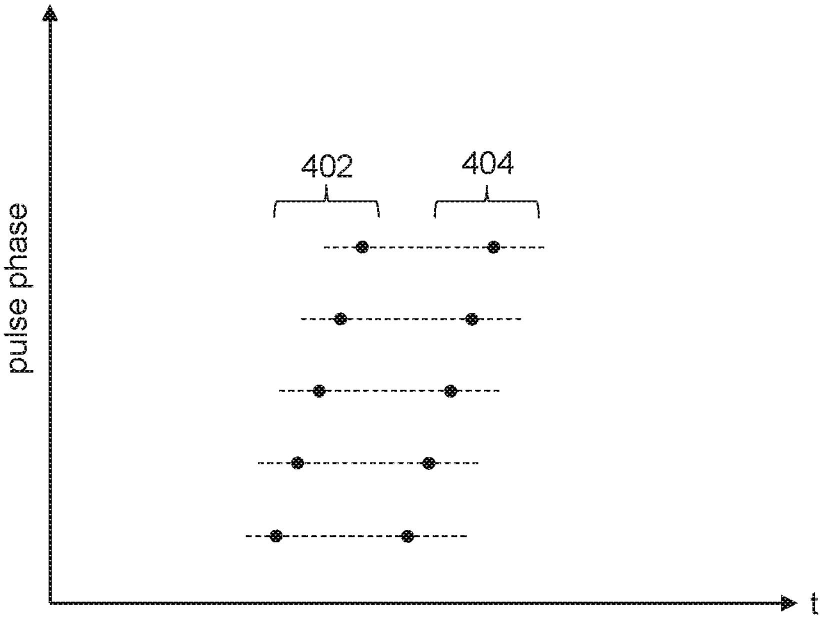
FIG. 4 illustrates a plot of pulse sequences against time for two successive heart cycles.

FIG. 4 illustrates a plot of pulse sequences in CRPS mode against time for two successive respiratory cycles 402, 404. The plot is a synchrogram plot of the type described previously with reference to FIGS. 2A and 2B, in which heartbeat instances, in time, on the x-axis is plotted with respect to a respiratory phase on the y-axis. In this example, each respiratory cycle contains five heartbeats. Each heartbeat in the first respiratory cycle 402 is in phase with a respective heartbeat in the subsequent, second respiratory cycle 404. Each heartbeat occurs at a particular time with respect to the onset of its respiratory cycle (that is, after a period of time has elapsed). The corresponding heartbeat of the subsequent respiratory cycle occurs at the same time with respect to the onset of its respiratory cycle. CRPS is evident with a repeat sequence over each respiratory cycle.

Returning to FIG. 3, in one or more examples, the controller 308 may be configured to operate in a free-running mode for one or more respiratory cycles and not provide a pacing signal or provide a pacing signal with no pulses. In this way, the controller 308 can monitor changes in the baseline heart rate, the baseline number of heartbeats per respiratory cycle or the baseline phase angles.

In one or more examples, the controller 308 may be calibrated. For example, sensor data including cardiological data may be monitored for a patient undergoing varying intensity levels of exercise to determine a set of baseline cardiological data for a range of respiration rates. The controller 308 may store the set of baseline cardiological data. In operation, the controller 308 may control the timing of the pulses of the pacing signal based on a respiration rate and the set of baseline cardiological data.

As outlined above, the controller 308 may be configured to control the timing of pulses in the pacing signal in accordance with the RSA factor and the CRPS factor to induce both RSA while maintaining CRPS. For example, the controller may control the timing of the pulses according to the first rate during inspiration, according to the second rate during expiration and with a fixed set of phase angles for a plurality of adjacent respiratory cycles or adjacent sets of respiratory cycles.

The controller 308 may further control the timing of pulses in the pacing signal according to methods known in the art. For example, the controller may control the timing of the stimulus signals according to a non-linear function which may be provided by, for example, a neuronal oscillator. The neuronal oscillator may be provided by analogue circuitry implementing, for example, a CPG, or by a digital simulation as disclosed in co-pending patent applications GB 1913050.9 and PCT/GB2020/052149.

The controller 308 is configured to provide the pacing signal based on the sensor data. The controller 308 may determine a RSA factor greater than 1 (ratio>1) to induce RSA via the pacing signal if the sensor data indicates that the cardiorespiratory system is functioning within a normal range with no significant increased stress or load. The controller may determine the RSA factor as equal to 1 (ratio equal to 1) if the sensor data indicates that the cardiorespiratory system is functioning under a temporary increased stress or load. The cardiorespiratory system may be functioning under a temporary increased stress when the patient physically exerts themselves, such as during exercise or lifting a heavy load. An increased stress may also be present when the patient is mentally stressed or following ingestion. Cardiorespiratory stress may also be dependent on one or more of: ambient temperature, O2 content (thin air), body position, dehydration, fever, starvation, noise, cold exposure, haemorrhage (menstrual cycle), psychological factors, immunological factors, pain and disease. The system may comprise one or more sensors to determine a level of one or more of these stress factors.

The controller 308 may determine a patient activity level based on the sensor data and determine the RSA factor dependent on the activity level. The activity level may indicate a temporary increased stress on the cardiorespiratory system.

The controller 308 may determine the patient activity level based on the respiratory data. For example, the controller may determine the activity level based on the minute ventilation data as described above and determine the RSA factor accordingly. As a further example, the controller may determine the RSA factor as greater than 1 if a respiration rate is less than or equal to a respiration rate threshold and determine the RSA factor as equal to 1 if the respiration rate is greater than the respiration rate threshold.

The sensor data may comprise cardiological data and the controller 308 may determine the patient activity level based on the cardiological data. For example, the controller may determine the RSA factor as greater than 1 if a heart rate is less than or equal to a heart rate threshold and determine the RSA factor as equal to 1 if the heart rate is greater than or equal to the heart rate threshold. The controller may also set the pacing mode dependent on a number of beats per respiratory cycle indicated by the respiratory data and the cardiological data.

The sensor data may comprise other data for indicating the patient activity level. For example, the controller 308 may receive sensor data comprising one or more of: cardiological data, pulse oximeter data, accelerometer data, body temperature data, perspiration data, camera data, adenosine triphosphate, ATP, levels, adrenaline levels or other data suitable for determining an activity level as known in the art. The other sensor data may be received from one or more corresponding sensors as are known in the art, such as an accelerometer, a pulse oximeter, a thermometer or a camera. The sensors may form part of the cardiac pacemaker system 300 or may be external to the system.

Figure 5:
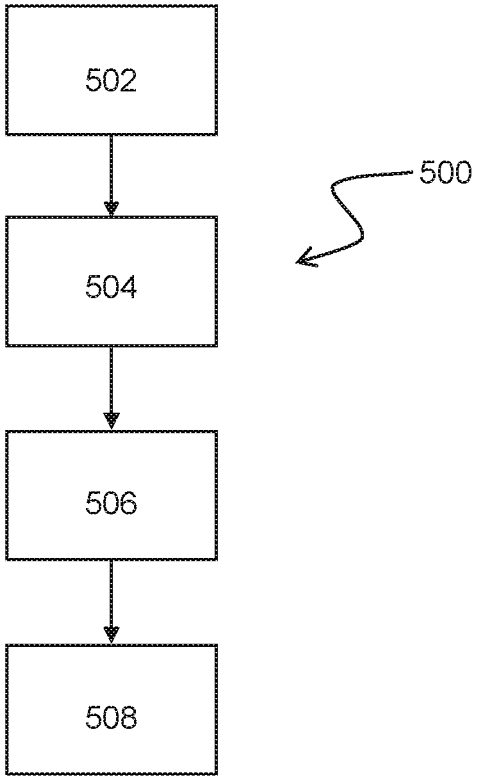
FIG. 5 illustrates a method for providing a pacing signal for pacing a heart of a patient.

FIG. 5 illustrates a method 500 for determining periodic or cyclical electrical stimulus signals temporarily modulated by a respiration signal, which may be performed by the controller described previously with reference to FIG. 3.

The method 500 for providing a pacing signal for pacing a heart of a patient, the method comprising:

receiving 502 sensor data comprising respiratory data;

determining 504 a RSA factor of a pacing signal based on the sensor data;

determining 506 a CRPS factor of the pacing signal based on the sensor data; and providing 508 the pacing signal in accordance with the RSA factor and the CRPS factor.

The use of the first input signal indicative of respiration to control the generation of the timing of the stimulus signals means that the method 500 provides direct physiological feedback.

A controller may be configured to perform any method described herein, including the method 500 as a computer-implementable method. The controller may comprise one or more processors and memory, the memory comprising computer program code configure to cause the processor to perform any method described herein.

There may be provided a computer program, which when run on a computer, causes the computer to configure any apparatus, including a controller for a cardiac pacemaker to perform any method disclosed herein. The computer program may be a software implementation. The computer may comprise appropriate hardware, including one or more processors and memory that are configured to perform the method defined by the computer program.

According to a further aspect of the disclosure there is provided a computer readable storage medium comprising computer program code configure to cause a processor to perform any computer-implementable method described herein. The computer readable storage medium may be a non-transitory computer readable storage medium. The computer program may be provided on a computer readable medium, which may be a physical computer readable medium such as a disc or a memory device, or may be embodied as a transient signal. Such a transient signal may be a network download, including an Internet download.

The invention claimed is:

1. A controller for a pacing device, configured to:

receive sensor data comprising respiratory data;

determine a respiratory sinus arrhythmia, RSA, factor of a pacing signal for inducing RSA in a patient based on the sensor data, wherein the RSA factor comprises one or more parameters of the pacing signal which provide a heart rate which is higher during an inspiration portion of a respiratory cycle than during an expiration portion of the respiratory cycle;

determine a cardio-respiratory phase synchronisation, CRPS, factor of the pacing signal for inducing CRPS in the patient based on the sensor data, wherein the CRPS factor comprises one or more parameters of the pacing signal which provide heartbeat pulses with respiratory phase values that repeat over an integer number of respiratory cycles; and provide, according to the respiratory cycle, the pacing signal for pacing a heart of a patient in accordance with the RSA factor and the CRPS factor.

2. The controller of claim 1, configured to:

determine a patient activity level based on the sensor data; and determine the RSA factor based on the patient activity level.

3. The controller of claim 1, wherein the sensor data further comprises one or more of: cardiological data, pulse oximeter data, accelerometer data, body temperature data, perspiration data, camera data, an adenosine triphosphate, ATP, level and an adrenaline level.

4. The controller of claim 1, wherein the controller is configured to determine the CRPS factor based on the RSA factor.

5. The controller of claim 1, wherein the controller is configured to provide the pacing signal in accordance with the RSA factor by controlling a timing of pulses in the pacing signal according to:

a first rate when the respiratory data indicates inspiration; and a second rate when the respiratory data indicates expiration, wherein the first rate is greater than the second rate.

6. The controller of claim 5, wherein the sensor data comprises cardiological data and the controller is configured to:

determine a baseline heart rate from the cardiological data; and set the first rate and second rate based on the baseline heart rate.

7. The controller of claim 6, wherein the controller is configured to set a ratio of the first rate to the second rate based on the baseline heart rate.

8. The controller of claim 7, wherein the controller is configured to:

determine a patient activity level based on the sensor data; and set a ratio of the first rate to the second rate based on the patient activity level.

9. The controller of claim 7, wherein the controller is configured to provide the pacing signal in accordance with the CRPS factor by controlling a timing of pulses in the pacing signal to correspond to a same set of respiratory phase angles in a repeat sequence over an integer number of respiratory cycles.

10. The controller of claim 9, wherein the controller is configured to set the first rate and the second rate to control the timing of the pulses in the pacing signal to correspond to the same set of respiratory phase angles in a repeat sequence over an integer number of respiratory cycles.

11. The controller of claim 10, wherein the sensor data comprises cardiological data and wherein the controller is configured to:

determine a patient activity level based on the sensor data;

determine the RSA factor based on the patient activity level;

set a ratio of the first rate to the second rate based on the RSA factor;

determine the CRPS factor as values of the first rate and second rate that provide the repeat sequence based on the ratio, a baseline heartrate of the sensor data and a respiratory rate of the respiratory data; and provide the pacing signal based on the first rate and the second rate.

12. The controller of claim 11, wherein the controller is configured to determine a first rate and a second rate that provide a modified baseline heart rate in the pacing signal to provide the repeat sequence.

13. The controller of claim 11, wherein the controller is configured to adjust the ratio of the first rate to the second rate to determine the CRPS factor as values of the first rate and second rate that provide the repeat sequence.

14. The controller of claim 9, wherein the controller is configured to determine the CRPS factor to reduce the number of respiratory cycles over which the pacing signal repeats.

15. The controller of claim 9, wherein the sensor data comprises cardiological data and the controller is configured to:

determine a baseline number of heartbeats per respiratory cycle and/or baseline phase angles based on the cardiological data and the respiratory data; and determine the set of respiratory phase angles based on the baseline number of heartbeats and/or the baseline phase angles.

16. A pacemaker system comprising:

the controller of claim 1;

one or more sensors for providing the sensor data; and one or more pacing electrodes for applying the pacing signal to the heart of the patient.

17. A method for providing a pacing signal for pacing a heart of a patient, the method comprising:

receiving sensor data comprising respiratory data;

determining a respiratory sinus arrhythmia, RSA, factor of a pacing signal for inducing RSA in a patient based on the sensor data, wherein the RSA factor comprises one or more parameters of the pacing signal which provide a heart rate which is higher during an inspiration portion of a respiratory cycle than during an expiration portion of the respiratory cycle;

determining a cardio-respiratory phase synchronisation, CRPS, factor of the pacing signal for inducing CRPS in the patient based on the sensor data, wherein the CRPS factor comprises one or more parameters of the pacing signal which provide heartbeat pulses with respiratory phase values that repeat over an integer number of respiratory cycles; and providing, according to the respiratory cycle, the pacing signal for pacing the heart of the patient in accordance with the RSA factor and the CRPS factor.

18. A computer program product storing executable instructions for performing the method of claim 17.

* * * * *